United States Patent
Santamarina et al.

(10) Patent No.: US 11,189,046 B2
(45) Date of Patent: Nov. 30, 2021

(54) COLORIMETRY AND IMAGE ANALYSIS DETERMINATION OF SPECIFIC SURFACE AREA

(71) Applicant: KING ABDULLAH UNIVERSITY OF SCIENCE AND TECHNOLOGY, Thuwal (SA)

(72) Inventors: Juan Carlos Santamarina, Thuwal (SA); Marisol Salva Ramirez, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 122 days.

(21) Appl. No.: 16/848,432

(22) Filed: Apr. 14, 2020

(65) Prior Publication Data
US 2020/0334845 A1 Oct. 22, 2020

Related U.S. Application Data

(60) Provisional application No. 62/836,875, filed on Apr. 22, 2019.

(51) Int. Cl.
G06T 7/62 (2017.01)
G06T 7/64 (2017.01)
G06T 7/90 (2017.01)

(52) U.S. Cl.
CPC .......... *G06T 7/62* (2017.01); *G06T 7/64* (2017.01); *G06T 7/90* (2017.01); *G06T 2207/10024* (2013.01)

(58) Field of Classification Search
CPC .... G06T 7/62; G06T 7/64; G06T 7/90; G06T 2207/10024; G01N 33/24; G01N 2201/0221; G01N 21/27
USPC ......................................................... 382/109
See application file for complete search history.

(56) References Cited

U.S. PATENT DOCUMENTS

| | | | | |
|---|---|---|---|---|
| 5,206,918 A | * | 4/1993 | Levene | ...................... G01J 3/46 |
| | | | | 382/110 |
| 2006/0050957 A1 | * | 3/2006 | Naccari | .............. G06K 9/00664 |
| | | | | 382/165 |
| 2011/0170786 A1 | * | 7/2011 | Naini | ......................... G06T 7/64 |
| | | | | 382/199 |
| 2014/0050397 A1 | * | 2/2014 | Badholm | .............. G06K 9/4652 |
| | | | | 382/165 |
| 2015/0117745 A1 | * | 4/2015 | Vapa | ......................... G06K 9/34 |
| | | | | 382/134 |
| 2019/0266788 A1 | * | 8/2019 | Huynh-Thu | ............ G06F 30/23 |

\* cited by examiner

*Primary Examiner* — Ali Bayat
(74) *Attorney, Agent, or Firm* — Patent Portfolio Builders PLLC

(57) ABSTRACT

A method for determining a specific surface area of a given material includes preparing plural samples of a dye and the given material; imagining the plural samples to generate digital images; calculating from the digital images, a saturation S for each of the plural samples; selecting a single saturation S value that corresponds to an excess dye condition; and calculating the specific surface area $S_s$ based on the single saturation S value, for the given material.

20 Claims, 18 Drawing Sheets

TABLE 1

| Technique | Description | Limitations | Standards |
|---|---|---|---|
| Direct Measurement | AFM or SEM area and weight measurements | Agglomeration of particles in dry conditions under vacuum. Difficult to distinguish individual particles | Not available |
| Crystallography analysis | Average weight, unit cell calculation by XRD and chemical analysis | Unit cell dimension uncertainties | Not available |
| Gas Adsorption | Physical adsorption BET, nitrogen | Pores smaller than the adsorbate. A dry technique which results in phyllosilicates collapse and closed pores. | ASTM B922-17 Standard Method for Metal Powder Specific Surface Area by Physical Adsorption. ASTM D4567-03(2013) Standard Test Method for Single-Point Determination of Specific Surface Area of Catalysts and Catalyst Carriers Using Nitrogen Adsorption by Continuous Flow Method ASTM C1274-12 Standard Test Method for Advanced Ceramic Specific Surface Area by Physical Adsorption. |

| Technique | Description | Limitations | Standards |
|---|---|---|---|
| | Water vapor adsorption | Pores smaller than the adsorbate. | Not available |
| | Ethylene Glycol Monoethyl Ether (EGME) | | |
| Adsorption of Molecule in Solution | Chemical adsorption of dyes, proteins and acids in solution and spectroscopy | Uncertainty in the contact area between the adsorbate and the adsorbent. | Not available |
| | Methylene blue adsorption by the spot and titration methods | | ASTM C837-1634(2014) Standard Method for Methylene Blue Index of Clay |
| | Protein Adsorption | | Not available |
| Calculation from Pore Size Distribution | Mercury intrusion porosimetry | Isolated pores, pores only accessible through smaller pores, pores smaller than the adsorbate. | Not available |
| Calculation from Permeability Measurements | Permeability test | Based on constitutive models (e.g. the Kozeny-Carman equation) | Not available |
| Inferred | Thermal, electrical, diffusiveness of x-ray diffraction patterns | | Not available |

TABLE 1

| Technique | Description | Limitations | Standards |
|---|---|---|---|
| Direct Measurement | AFM or SEM area and weight measurements | Agglomeration of particles in dry conditions under vacuum. Difficult to distinguish individual particles | Not available |
| Crystallography analysis | Average weight, unit cell calculation by XRD and chemical analysis | Unit cell dimension uncertainties | Not available |
| Gas Adsorption | Physical adsorption BET, nitrogen | Pores smaller than the adsorbate. A dry technique which results in phyllosilicates collapse and closed pores. | ASTM B922-17 Standard Method for Metal Powder Specific Surface Area by Physical Adsorption. ASTM D4567-03(2013) Standard Test Method for Single-Point Determination of Specific Surface Area of Catalysts and Catalyst Carriers Using Nitrogen Adsorption by Continuous Flow Method ASTM C1274-12 Standard Test Method for Advanced Ceramic Specific Surface Area by Physical Adsorption. |

FIG. 1A

| Technique | Description | Limitations | Standards |
|---|---|---|---|
| Adsorption of Molecule in Solution | Water vapor adsorption | Pores smaller than the adsorbate. | Not available |
| | Ethylene Glycol Monoethyl Ether (EGME) | | Not available |
| | Chemical adsorption of dyes, proteins and acids in solution and spectroscopy | Uncertainty in the contact area between the adsorbate and the adsorbent. | |
| | Methylene blue adsorption by the spot and titration methods | | ASTM C837-1634(2014) Standard Method for Methylene Blue Index of Clay |
| | Protein Adsorption | | Not available |
| Calculation from Pore Size Distribution | Mercury intrusion porosimetry | Isolated pores, pores only accessible through smaller pores, pores smaller than the adsorbate. | Not available |
| Calculation from Permeability Measurements | Permeability test | Based on constitutive models (e.g. the Kozeny-Carman equation) | Not available |
| Inferred | Thermal, electrical, diffusiveness of x-ray diffraction patterns | | Not available |

FIG. 1B

| Dye | pH, time and concentration effects |
|---|---|
| Hemoglobin | At a neutral pH (7): increase ionic strength and adsorption.<br><br>Protein adsorption in clay is induced by electrostatic interactions. The adsorption is similar to the behavior of a cation exchange. |
| Rhodamine-B | Adsorption in Moroccan clays depends on time, temperature, initial concentration and the pH of the solution.<br><br>Similarly, adsorption in kaolinite and sodium montmorillonite and show a good adsorption capacity at a pH of 7. |
| Crystal violet | The adsorption in kaolinite is highly dependent on the adsorbent dose, contact time, pH, initial dye concentration, stirring speed and the temperature.<br><br>Variations in the adsorption kinetics in silica result from different pH levels.<br><br>Maximum adsorption occurs at a pH of 7.8 and the adsorption increases with adsorbent concentration.<br><br>As the pH increases, more negatively charged surfaces are available and results in a decrease in the repulsion between the positively charged dye molecules and the adsorbent. |
| Methylene blue | Adsorption is pH dependent with some dyes more susceptible to changes in pH levels.<br><br>A neutral pH of approximately 7.0 enhances adsorption. The pH-dependent charge of particle edges may also influence adsorption by electrostatic attraction or repulsion.<br><br>The pH at point zero charge shows a maximum adsorption of cationic dyes as Methylene blue and Rhodamine-B. |

FIG. 5

TABLE 3

| Specimens | Ss [m²/g] | Mean grain size [μm] | LL dw [%] | LL brine [%] | LL ker [%] | Classification |
|---|---|---|---|---|---|---|
| Bentonite 1 (Slm) | 532 | 0.07 | 340 | 102 | 49 | F(F)-IH |
| Bentonite 2 (HTC) | 593 | 0.07 | 390 | 79 | 51 | F(F)-IH |
| Bentonite 3 (KSA 1) | 544 | 0.07 | 320 | 92 | 39 | F(F)-LH |
| Bentonite 4 (KSA 2) | 550 | 0.07 (*) | 308 | 65 | 49 | F(F)-IH |
| Kaolinite 2 (RP2) | 67 | 0.36 | 52 | 46 | 76 | F(F)-IH |
| Kaolinite 1 (SA1) | 34 | 0.36 (*) | 48 | 52 | 67 | F(F)-HI |
| Red Sea Sediments | 24 | 2.0 | 36.8 | 18.46 | 5.7 | F(F)-NH |
| Diatoms (CG1) | 5 | | | | | |
| Silica Flour | 0.5 | 20 (*) | 31 | 26 (*) | 28 (*) | F(F)-NL |
| Illite | 56 | 0.5 (*) | 42.62 | | | |
| Attapulgite (Eastchem) | 160 | | 67 | | | |

FIG. 6

TABLE 4

| Dye | Methylene Blue | Rhodamine B | Crystal Violet | Hemoglobin |
|---|---|---|---|---|
| Structure | (structure) | (structure) | (structure) | (structure) |
| Characteristics | $C_{16}H_{18}ClN_3S$<br>contact area 25-130 $Å^2$ per molecule<br>molecular weight 319.87 g/mol<br>cationic<br>water soluble<br>maximum absorption light 670 nm | $C_{28}H_{31}ClN_2O_3$<br>contact area 110 $Å^2$ per molecule<br>molecular weight 479.016 g/mol<br>cationic<br>water soluble<br>fluorescence absorption 554 nm, emission 576 nm | $C_{25}N_3H_{30}Cl$<br>contact area 120 $Å^2$ per molecule<br>molecular weight 407.986 g/mol<br>cationic<br>water soluble<br>maximum absorption 590 nm in water | contact area 3800 $Å^2$ per molecule<br>molecular weight 68000 g/mol<br>cationic/anionic<br>water soluble<br>absorption 420 nm |

FIG. 7

COLORIMETRY AND IMAGE ANALYSIS DETERMINATION OF SPECIFIC SURFACE AREA

CROSS-REFERENCE TO RELATED APPLICATIONS

This application claims priority to U.S. Provisional Patent Application No. 62/836,875, filed on Apr. 22, 2019, entitled "SPECIFIC SURFACE BY COLORIMETRY AND IMAGE ANALYSIS," the disclosure of which is incorporated herein by reference in its entirety.

BACKGROUND

Technical Field

Embodiments of the subject matter disclosed herein generally relate to a system and method for determining the specific surface area of a material based on colorimetry and image analysis, and more particularly, to measuring the color saturation of a material mixed with a dye and calculating the specific surface area from this parameter.

Discussion of the Background

Grain size is an inherent scale of the particle materials. It has implications on particle governing forces and leads to a fundamental distinction between coarse and fine-grained soils. The specific surface area, defined by the amount of surface area for a given soil mass, determines the balance between (1) surface related forces, such as the electrical and van der Waals attraction, and (2) gravimetric, skeletal forces. Specific surface area measurements can capture the effect of the particle size and slenderness in one measurement.

The specific surface area in fine-grained sediments affects the fabric formation, supports coupling mechanisms and governs the conduction in such material. A larger surface area indicates higher drag forces along the pore walls and lower hydraulic conductivity. It also controls the adsorption and retardation during chemical diffusion, which has significant implications on soil behavior, particularly in the areas of electrical conductivity and permittivity, compressibility, pore size, swelling and shrinkage.

The specific surface area also has implications in the effectiveness of mineral separation, inhibits froth flotation, magnetic and electrical separation process due to particle interactions. The liquid limit frequently used in soil classification matters reflects the specific surface area of the soil, the thickness of the double layer (determined by the electrons and atoms), and the soil fabric. Thus, knowing the specific surface area for a given material is desirable in many fields.

Current specific surface area measurement methods are time-consuming, e.g., determining the chemical adsorption of dyes with a spectrometer or require expensive equipment like a gas adsorption Brunauer-Emmett-Teller (BET) system. Less expensive methods based on dye adsorption have ill-defined end points and remain time-consuming, particularly for high specific surface area materials.

The identification of high specific surface area materials during soil characterization is critical for the design, construction, and service-life phases in engineering projects. Routine geotechnical characterization surveys rarely include measurements of the specific surface area despite its critical role in the behavior of fine-grained sediments.

Thus, there is a need for a new method for determining the specific surface area of any given material quickly, accurately and in a simple manner.

BRIEF SUMMARY OF THE INVENTION

According to an embodiment, there is a method for determining a specific surface area of a given material. The method includes preparing plural samples of a dye and the given material, imagining the plural samples to generate digital images, calculating from the digital images, a saturation S for each of the plural samples, selecting a single saturation S value that corresponds to an excess dye condition, and calculating the specific surface area $S_s$ based on the single saturation S value, for the given material.

According to another embodiment, there is a portable device for determining a specific surface area of a given material. The portable device includes a source light configured to illuminate plural samples of a dye and the given material, a digital camera configured to imagine the plural samples to generate digital images, and a processor that is connected to the digital camera. The processor is configured to calculate from the digital images, a saturation S for each of the plural samples, select a single saturation S value that corresponds to an excess dye condition, and calculate the specific surface area $S_s$ based on the single saturation S value, for the given material.

According to still another embodiment, there is a method for determining a specific surface area of a material. The method includes imagining plural samples of a dye mixed with the material to generate digital images, calculating from the digital images, saturation S values for the plural samples, calculating a single saturation S value that corresponds to an excess dye condition, and calculating the specific surface area $S_s$ based on the single saturation S value, for the given material.

BRIEF DESCRIPTION OF THE DRAWINGS

For a more complete understanding of the present invention, reference is now made to the following descriptions taken in conjunction with the accompanying drawings, in which:

FIGS. 1A and 1B illustrate traditional methods for measuring the specific surface area of a material;

FIG. 5 illustrates the sensitivity to pH, time and concentration effects of different dye adsorption in clays;

FIG. 6 illustrates sediment properties, mineralogy, specific surface areas, grain sizes, liquid limits, and classifications for various samples used to calculate the specific surface area;

FIG. 7 illustrates dye properties for Methylene Blue, Rhodamine B, Crystal Violet, and Hemoglobin, their structure and characteristics such as contact area, molecular weight, cationic/anionic, and light absorption peak in a water solution;

DETAILED DESCRIPTION OF THE INVENTION

Figure 2A:
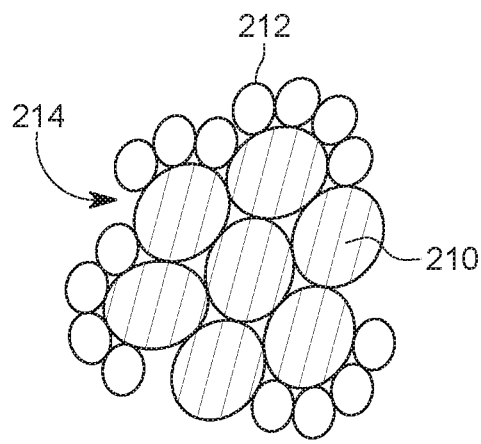
FIGS. 2A to 2C illustrate the adsorption process between a dye and a given material, with the formation of a full layer of dye around the material.

The following description of the embodiments refers to the accompanying drawings. The same reference numbers in different drawings identify the same or similar elements. The following detailed description does not limit the invention. Instead, the scope of the invention is defined by the appended claims. The following embodiments are discussed, for simplicity, with regard to a given material that is mixed with one of four dyes and a portable device (smartphone) is employed to determine the specific surface area of the given material. However, the embodiments to be discussed next are not limited to these four dyes or to a portable device, but they may be implemented for any other dye and for any other system that has a digital camera, a light source, and a processor.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to an embodiment, an alternative method, based on colorimetry, is introduced for determining the specific surface area of a given material and the method is implementable with, for example, a smartphone to accurately measure the specific surface area of fine-grained soils. The method may also analyze different dyes to explore the effects of dye molecule size and shape, adsorption time-dependence, and pH effects on the adsorption process.

Prior to discussing this novel method, a quick review of the existing methods for determining the specific surface area of a material is believed to be in order. The specific surface area of a material is a property of solids defined as the total surface area of a material per unit of mass. Table 1 in FIGS. 1A and 1B illustrate both direct and indirect specific surface area measurement techniques and includes key limitations of the existing methods. Adsorption is the most frequently used method for measuring the specific surface area of a given material. However, these methods are all expensive and/or time-consuming. The water-based methods are ideal for swelling clays and fine-grained soils and can measure the internal surface area of phyllosilicates.

Previous dye adsorption studies used the titration/spectrometer method with Methylene blue, Crystal violet, Methyl red, Congo red, and Orange II dyes. Other studies used proteins such as hemoglobin as the dye substance. The Methylene blue spot test is a less expensive method, but it can be time-consuming, and it has a high risk of operator error due to the ill-defined end-point. Some advantages related to these methods are that these methods apply to a wide range of minerals, provide both the external and internal specific surface areas, and have a relatively fast adsorption time for most solids.

The adsorption process on which most of these methods rely is now briefly discussed. Clays are negatively charged because of termination sites. To satisfy electro-neutrality, counterions are attached to their surface by Coulombic attraction. When the particle is wet, precipitated ions dissociate and hydrate. The distribution of cations around the particle depends on the properties of the pore fluid (permittivity, ion concentration, and valence) according to the double layer theory.

Dye adsorption uses cationic dyes, which dissociates into positively charged ions in an aqueous solution. During adsorption, counterions on the surface of the clay are exchanged by the cationic dye molecules. Ionic Coulombic attraction develops between the dye molecule and the mineral surface; this is called chemisorption. A monolayer of absorbed cationic dye molecules forms around the surface of the clay particle. Thus, if one can calculate the amount or mass of dye molecules that have attached to the clay particles only for one monolayer, it is possible to determine the specific surface area of the clay particles as now discussed.

This technique is useful to measure the specific surface area if the amount of the adsorbate (e.g., dye) and contact area per molecule of the adsorbate are known. In this respect, equation (1) can be used to calculate the specific surface area $S_s$ of the dye adsorption in an aqueous solution as:

$$S_s = \frac{1}{M_{dye}} A_v S_{a_{dye}} \frac{m_{dye}}{m_{soil}}, \quad (1)$$

where $M_{dye}$ is the molecular weight of the dye (g/mol), $A_v$ is Avogadro's number ($6.02 \times 10^{23}$ molecules/mol), $S_{a_{dye}}$ is the contact area between the dye and soil particles and this quantity is known in the art, and $m_{dye}$ and $m_{soil}$ (g) correspond to the mass of dye and soil added to the mixture up to the point where the full adsorbate film (monolayer) is created. This point is identified by an excess of dye as discussed later.

Figure 2B:
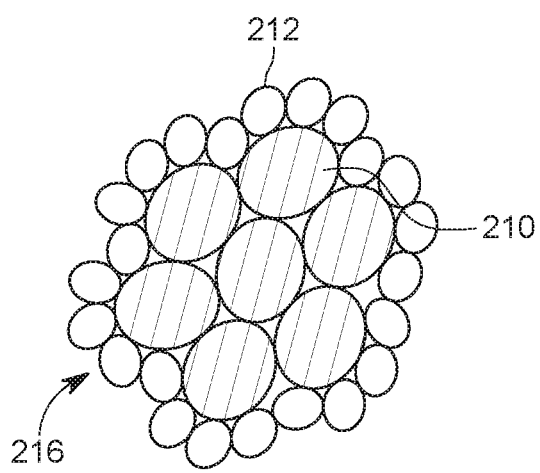
Figure 2C:
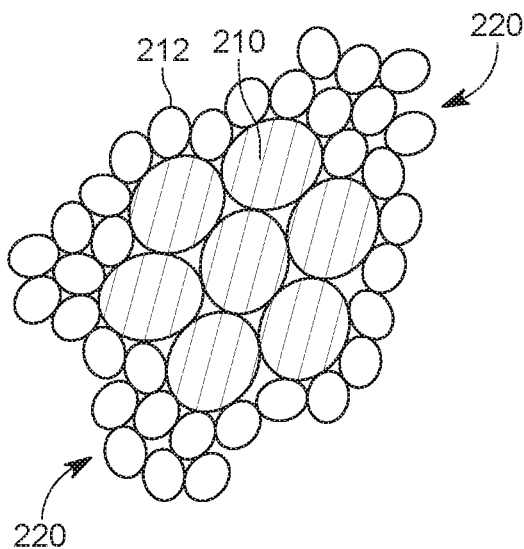

Determining when the full adsorbate film is formed is one of the points where the previous method fails. This issue is illustrated in a cartoon type manner in FIGS. 2A to 2C. FIG. 2A shows the material particles (e.g., clay particles) 210 being partially covered by the dye molecules 212. However, there are areas 214 where the material particles 210 are not yet covered by the dye molecules 212. Thus, at this point in time, equation (1) will not produce an accurate result for the specific surface area of the material particles 210. This situation changes in FIG. 2B, where the dye molecules 212 have fully covered the material particles 210, forming a single layer 216 (the monolayer). Note that in FIG. 2C, there are areas 220 in which the dye molecules 212 are forming a second layer. The situation illustrated in FIG. 2C is also not conducive to an accurate estimation of the specific surface area when using equation (1). The situation illustrated in FIG. 2B provides the ideal arrangement of the dye particles relative to the material particles, i.e., a single full layer 216 of the dye formed around the material. However, to determine the case when the single layer 216 of the dye material has formed, just before the case illustrated in FIG. 2C is the point where the existing methods fail. The condition shown in FIG. 2C is called the excess dye condition.

Previous research has extensively focused on dye adsorption in water treatment and waste management to remove dyes that are considered pollutants using clays as a low-cost solution. Clay minerals show a strong affinity for both cationic and anionic dyes. Ion-exchange dominates the adsorption of dyes onto clay minerals. Therefore, the adsorption capacity varies with the pH. When the ion exchange capacity is high (CEC=1.16 meq/g), as for methylene blue adsorption, the molecules adsorb in a tilted orientation and are not parallel to the surface. This tilted orientation of the dye molecules can result in inaccurate calculations of a larger molecular coverage and specific surface area when compared to the actual values.

Figure 3:
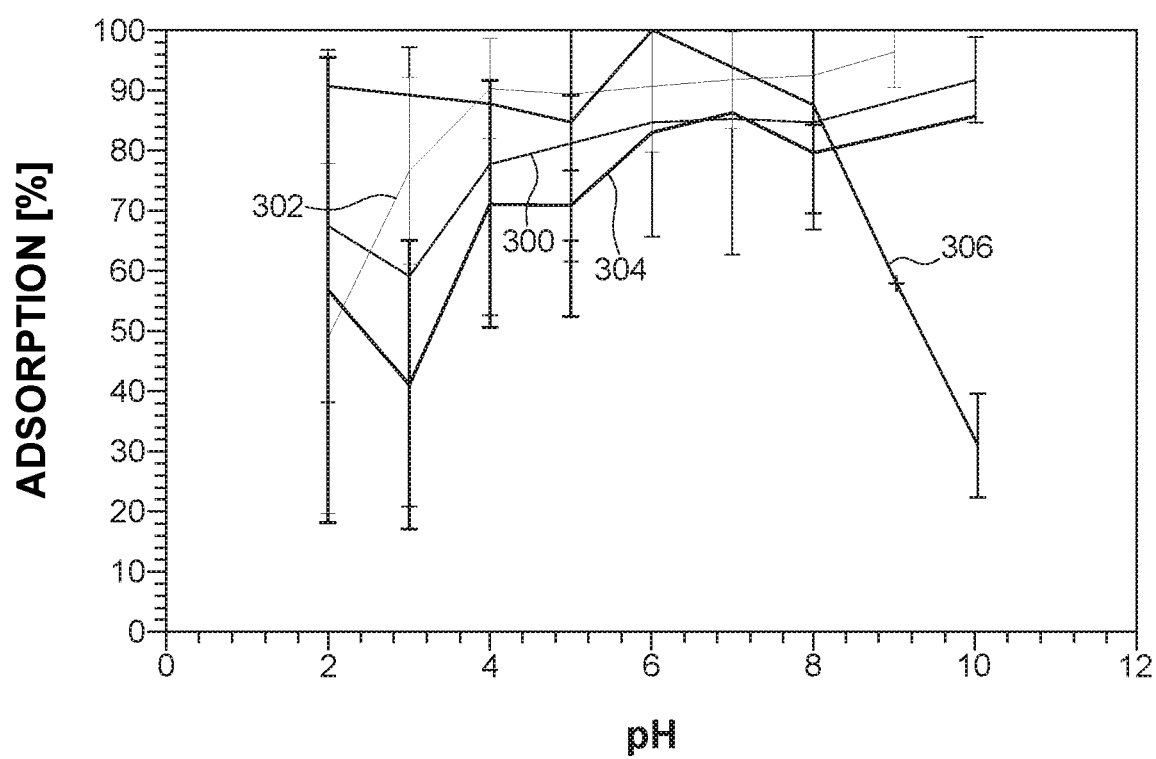
FIG. 3 illustrates the pH-dependent adsorption for Methylene blue, Crystal violet, Rhodamine B and Hemoglobin.
Figure 4:
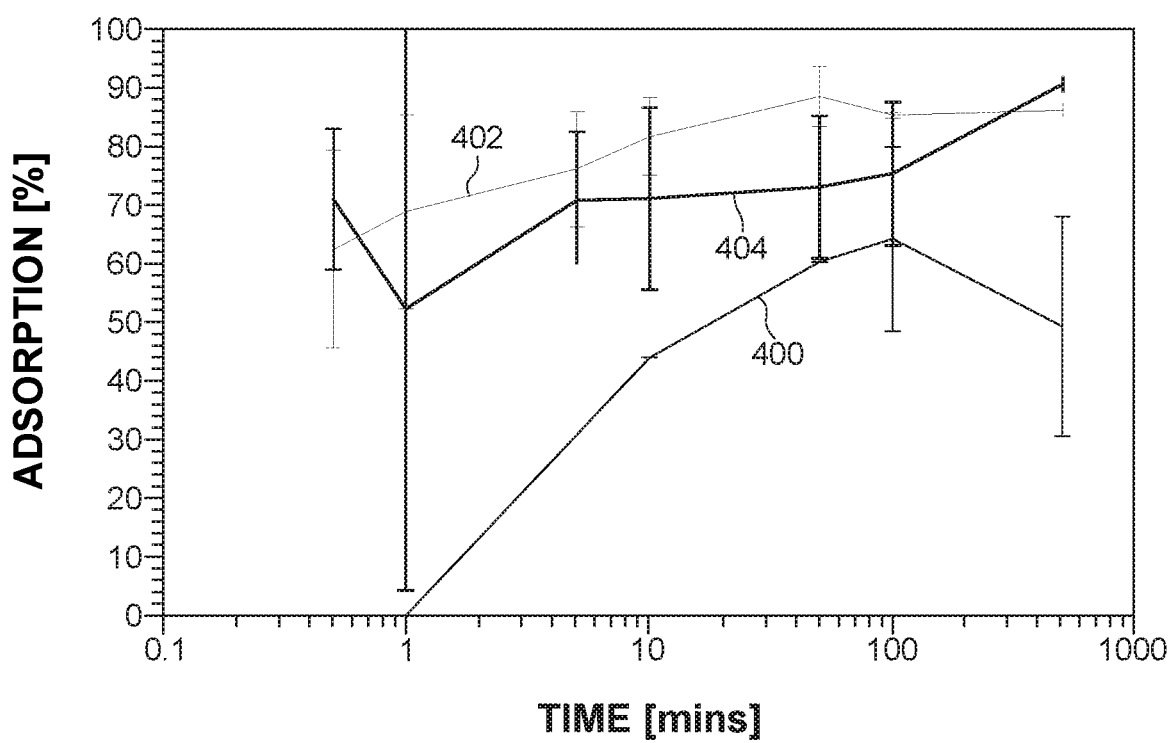
FIG. 4 illustrates the time dependent adsorption for Methylene blue, Crystal violet, Rhodamine B and Hemoglobin.

In this regard, FIG. 3 shows the change in the adsorption for different types of dye molecules (methylene blue curve 300, crystal blue curve 302, rhodamine B curve 304, and hemoglobin 306) in clay as a function of the pH and FIG. 4 shows the change in the adsorption for different types of dye molecules (methylene blue curve 400, crystal blue curve 402, and rhodamine B curve 404) in clay as a function of time. In general, it is observed that the adsorption increases with time (see FIG. 4), but reaches a plateau controlled by the adsorbent dosage. This means that increases in the steering speeds result in faster adsorption times. Methylene blue (MB) tests reach the plateau after 25 minutes, Crystal violet (CV) reached the plateau within 20 minutes, and Rhodamine-B (RB) reached the plateau within 30 minutes.

The sensitivity to pH, time and concentration effects on the dye adsorption has been extensively studied as illustrated in Table 2 in FIG. 5. The mechanisms and kinetics of dye adsorption in various adsorbents depend on the chemical nature of the materials and various physicochemical experimental conditions. These conditions should be all taken into consideration when dealing with adsorption problems. Thus, in one embodiment, for a higher adsorption efficiency, the pH should be the buffer pH and the time of adsorption should be large enough to reach the plateau.

The inventors have observed that all these factors can be taken advantage of within a digital image colorimetry method for more accurately determining the specific surface area of a material. The colorimetry relies on measuring light properties that are associated with the color of the light emitted by a material. More specifically, the color is a property of light and corresponds to the visible range of the electromagnetic spectrum, where different colors correspond to different wavelengths of between 400-700 nm, from violet to red.

Digital cameras have red-green and green-blue filters to separate the received light intensity into red, green and blue, which form the RGB channels. The digital cameras record the corresponding intensities in each pixel, in these three spectral bands. Reconstruction of a full-color image combines the information from the three channels. The RGB is an additive color model that senses and displays images of electronic systems. Each color is a linear combination of red, green and blue values and varies from zero (black) to full intensity (white). For each basic color, the value is an integer between 0 and 255 (for 8 bits) normalized by dividing to 255.

The hue, saturation, and value (HSV) is an alternative representation of the RGB model, where the colors appear around a central axis. The hue H is an angle that specifies the position of the pure color in the color wheel, as hue increases from 0 to 1, and the color transitions from red to orange, yellow, green, cyan, blue, magenta, and finally back to red. The saturation S describes the colorfulness relative to its own brightness. For example, pure red is fully saturated when S=1, tints of red have S<1, and white is described by S=0. The value V corresponds to the lightness and describes the darkness of the color where black is described by V=0.

The conversion from the RGB system to the HSV system is described by the following equations:

$$C_{max} = \max(\bar{R}, \bar{G}, \bar{B}) \quad (2)$$

$$C_{min} = \min(\bar{R}, \bar{G}, \bar{B}) \quad (3)$$

$$\Delta = C_{max} - C_{min} \quad (4)$$

$$H = \begin{cases} 60° \times \left(\frac{G-B}{\Delta} \mod 6\right), & C_{max} = R \\ 60° \times \left(\frac{B-6}{\Delta} + 2\right), & C_{max} = G \\ 60° \times \left(\frac{R-G}{\Delta} + 4\right), & C_{max} = B \end{cases} \quad (5)$$

$$S = \begin{cases} 0, & C_{max} = 0 \\ \frac{\Delta}{C_{max}}, & C_{max} \neq 0 \end{cases} \text{ and} \quad (6)$$

$$V = C_{max}, \quad (7)$$

where equations (2) to (4) define the intermediary quantities of a maximum value of the RBG colors $C_{max}$, a minimum value $C_{min}$, and a chroma $\Delta$, and equations (5) to (7) define the hue H, saturation S, and the value V as a function of the intermediary values.

Digital image colorimetry consists of image acquisition followed by an analysis of the channel composition for each pixel, in the HSV model discussed above. The accuracy in digital image colorimetry overcomes limitations associated with direct visual observations. In particular, the inventors have observed that changes in the saturation S values track the changes in the dye concentration as the monolayer 216 is formed due to the adsorption process and a sudden change in the saturation S corresponds to the excess dye condition. Based on this observation, by imagining the adsorption process of a dye onto a given material, and by recording the colors associated with this process, it is possible to determine when the full layer 216 is formed based on the recorded saturation S. This process is now discussed in more detail.

The inventors have analyzed 11 fine-grained soils composed of different mineralogies and origins. Table 3 in FIG. 6 presents the mean grain size, specific surface, liquid limit and classification by sensitivity to pore fluid chemistry of the 11 studied samples. The specific surface areas $S_s$ for these soils varies from 1 to 500 m²/g, as also illustrated in FIG. 6.

Three dyes, Methylene blue, Crystal violet, Rhodamine-B and a protein, Hemoglobin, were tested on these samples to explore the effect of the molecular size and shape, adsorption time dependency, and pH effects on the adsorption process. Dye selection considers different light adsorption wavelengths, contact areas, and geometries, as illustrated in Table 4 in FIG. 7. The selection of cationic dyes with regular 3D geometry in comparison to the 1D Methylene blue chain decreases the contact area uncertainty associated with molecular orientation during adsorption. Table 4 presents the structure and significant properties of all tested dyes.

Figure 8A:
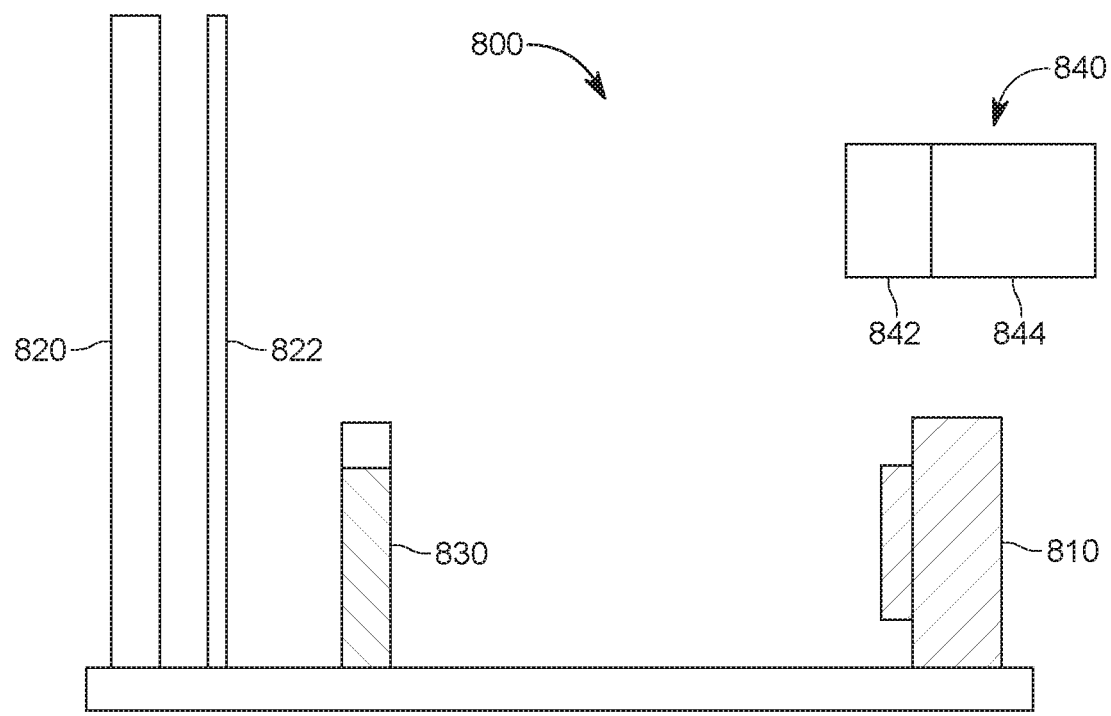
FIGS. 8A and 8B illustrate experimental setups for color analysis for Methylene blue and Rhodamine B dyes.
Figure 8B:
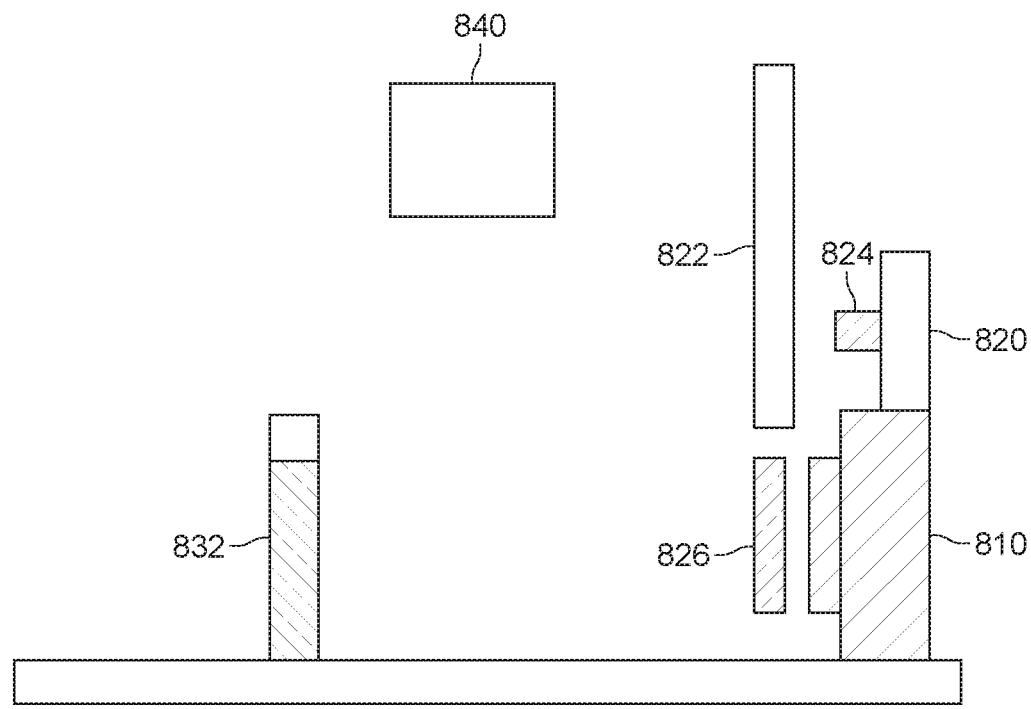

The system used to calculate the specific surface area of the soils in the presence of the various dyes is shown in FIG. 8A for the first three dyes and in FIG. 8B for the last dye, i.e., the Rhodamine B. The system 800 includes a digital camera 810, a light panel source 820, and a diffusor 822. The test sample 830 was placed between the diffusor 822 and the digital camera 810 and was selected to be the methylene blue. For the Rhodamine-B sample 832, the same system 800 was used, but with the addition of a green light emitted diode (LED) 824 and a band pass filter 826 to measure the fluorescence, as illustrated in FIG. 8B. A control system 840, that may include a processor 842 and a memory 844, are also provided for coordinating these elements and calculating the saturation S and eventually the specific surface area $S_s$.

Figure 9:
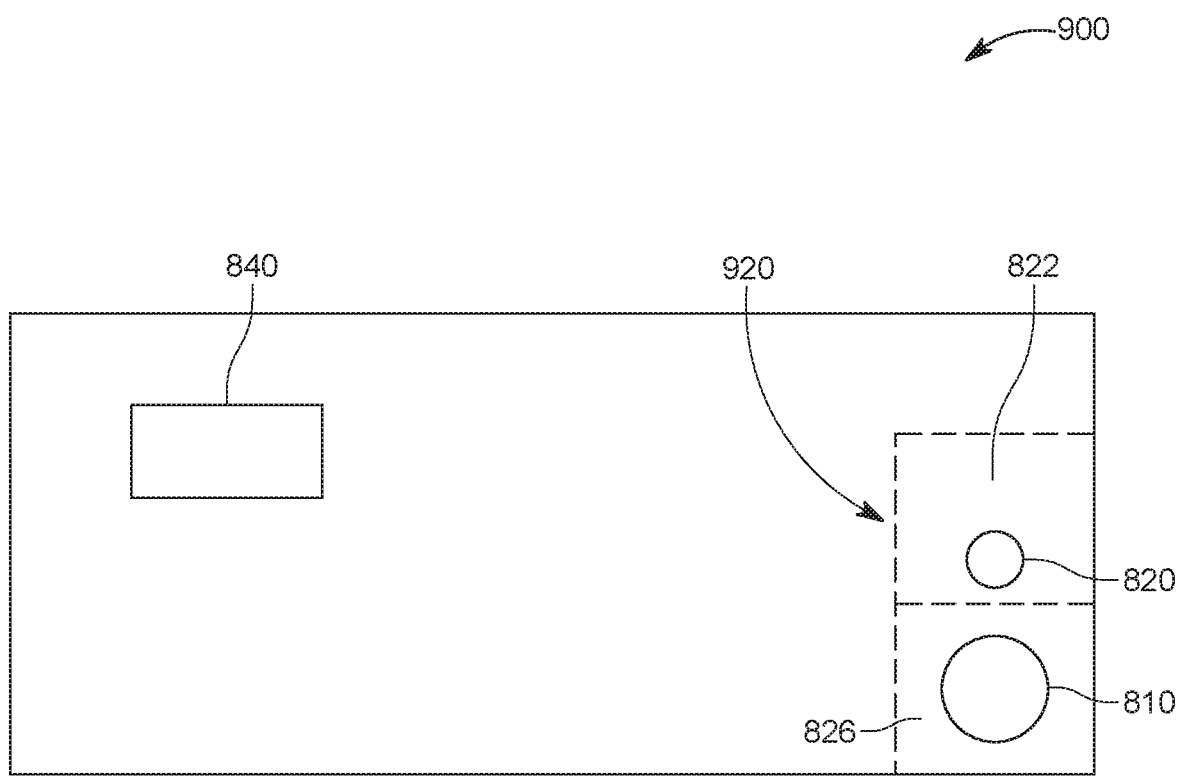
FIG. 9 illustrates a portable device that can be used to perform the color analysis of various samples for determining the specific surface area of a material.

As the recent revolution in sensors has opened the door to affordable technology for all technical areas, a high capacity smartphone, which is widely available, include most of the above elements necessary for image analysis and colorimetry. In another words, a smartphone or similar device 900, as illustrated in FIG. 9, may be configured to use its own control system 840 to coordinate the digital camera 810 and the source light 820. A clip-on attachment 920 may be added to the smartphone to provide the diffusor 822 and, if necessary, the filter 826. In this way, the user of the smartphone can take pictures of the soil material while reacting with the selected dye and by using a dedicated application implemented on the smartphone, the user may calculate the specific surface area for that soil material. This application uses the HSV model described by equations (2) to (7) to determine the specific surface area.

Figure 10A:
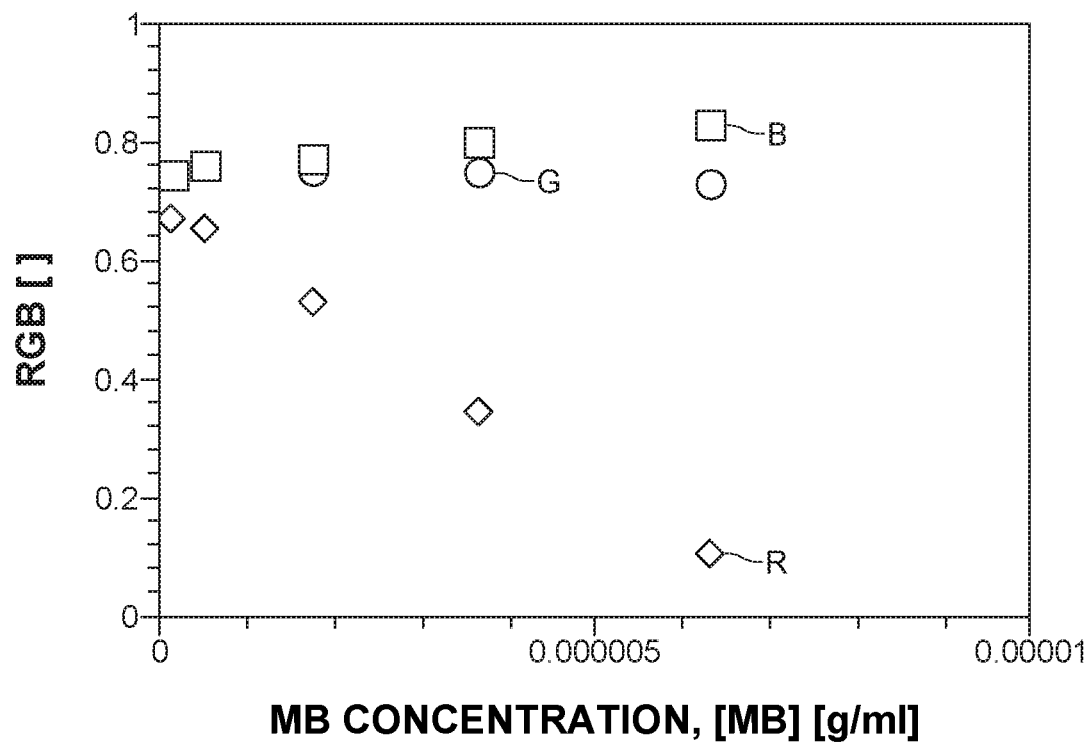
FIGS. 10A and 10B illustrate the mean RGB values recorded with a digital camera for the Methylene blue and Rhodamine B dyes when mixed with a given sample.
Figure 10B:
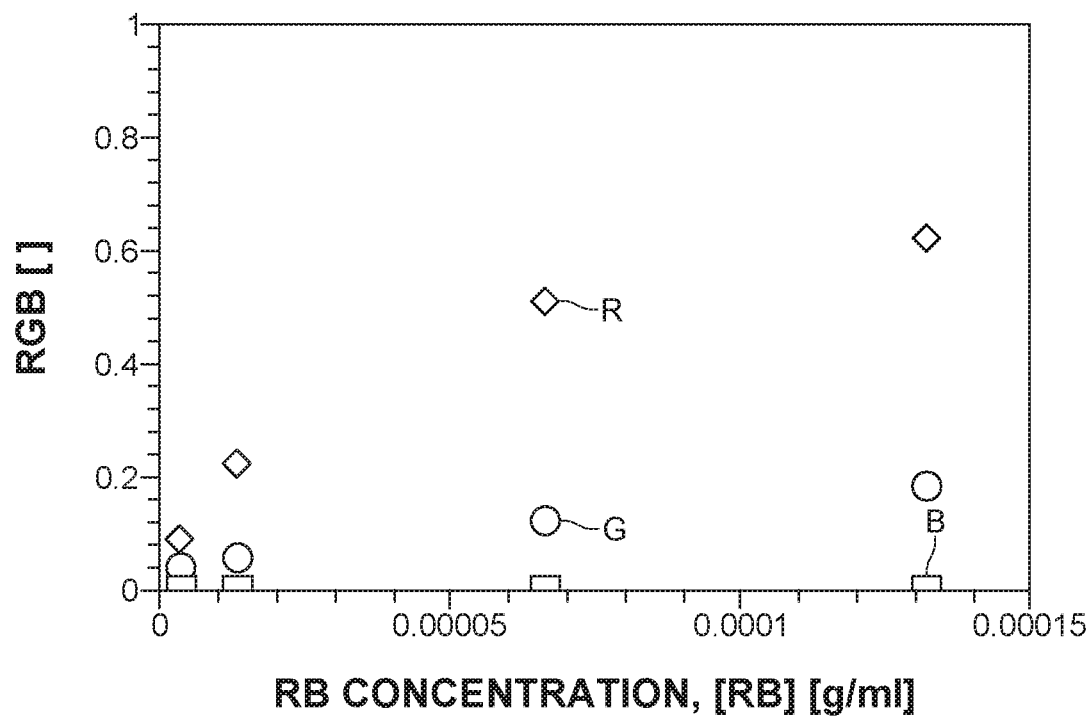

The mean RGB values obtained with the smartphone 900 for the two samples 830 and 832, which are shown in FIGS. 8A and 8B, are illustrated in FIGS. 10A and 10B, respectively. The mean RGB values are illustrated in FIGS. 10A and 10B as a function of the MB and RB dye concentrations, respectively.

Figure 11:
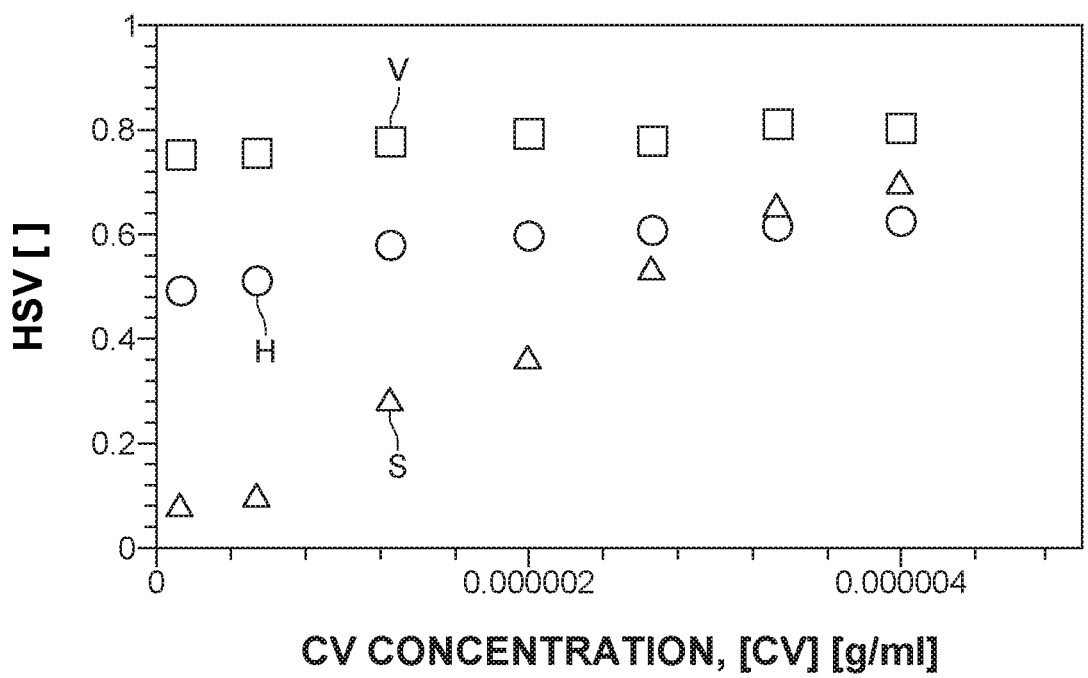
FIG. 11 shows the HSV values for different dye concentrations, obtained from the RGB values.
Figure 12:
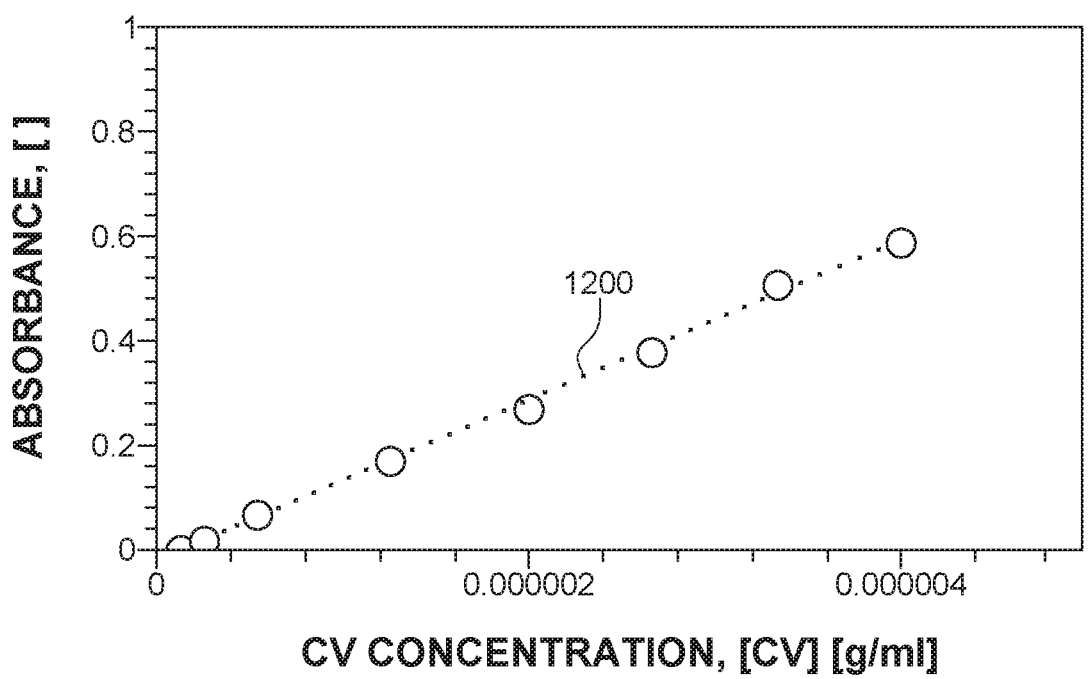
FIG. 12 illustrates the absorbance for different dye concentrations at 430 nm.

The system was calibrated for all four dyes used in these tests for different concentrations. The saturation S increases with the dye concentration, at low concentrations, as illustrated in FIG. 11. FIG. 11 also plots the hue H and the value V for various CV dye concentrations. Note that all the S, H and V values shown in these figures were calculated with the smartphone 900, which used its digital camera and its light source to record the RGB data, and then used equations (2) to (7), which were programmed into the application, to calculate the corresponding H, S, and V values. The inventors have noted that the saturation S's increase observed in FIG. 11 is similar to the light absorption curve 1200 for the dye, which is illustrated in FIG. 12, and is described by the Beer and Lambert equation, which is given by:

$$A = -\ln\left(\frac{I_s}{I_0}\right), \qquad (8)$$

where A is the absorption, $I_s$ is the transmitted light, and $I_o$ is the incidence light.

Thus, based on this observation, the inventors have developed a method in which the saturation S of a dye is plotted as a graph and when the saturation S experiences a sudden change, that change indicates that the first full layer 216 around the soil material has been obtained, i.e., the excess dye condition has been reached. Thus, according to this method, the value of the ratio of the dye/soil mass can be accurately extracted from the graph of the saturation S and it can be used by the application, in equation (1), to calculate the specific surface area of the tested soil. This method is now discussed with regard to the samples noted above.

A high concentration dye solution (e.g., MB 5 g/L, CV 2 g/L, RB 0.05 g/L and HG 5 g/L) was initially prepared. Multiple test tubes were filed with 1 g of dry soil sample, previously washed to remove any salts, which was dispersed in 10 ml of deionized water. Various concentrations of the dye solution were added to the various test tubes. The dye solution and the soil sample were mixed over 5 minutes by using a vortex or steering plate. The slurries in the test tube were centrifuged for 10 minutes at 10,000 rpm to force sedimentation. Next, 3 ml of the supernatant was placed into a transparent cuvette for the various samples with the different dye concentrations. Then, a digital picture of each sample was taken with the smartphone 900.

Figure 13A:
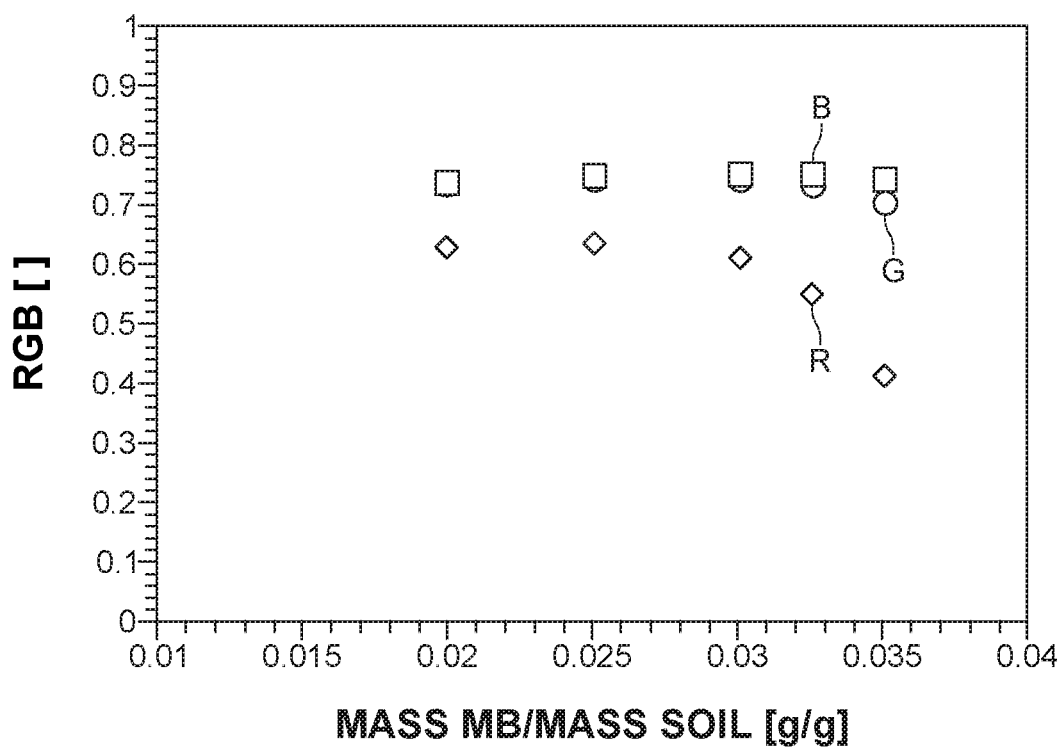
FIG. 13A illustrates the RGB values obtained from the image analysis for a Kaolinite (2) sample with Methylene Blue (MB) adsorption and FIG. 13B illustrates the corresponding saturation S values for various dye to material mass ratios.
Figure 13B:
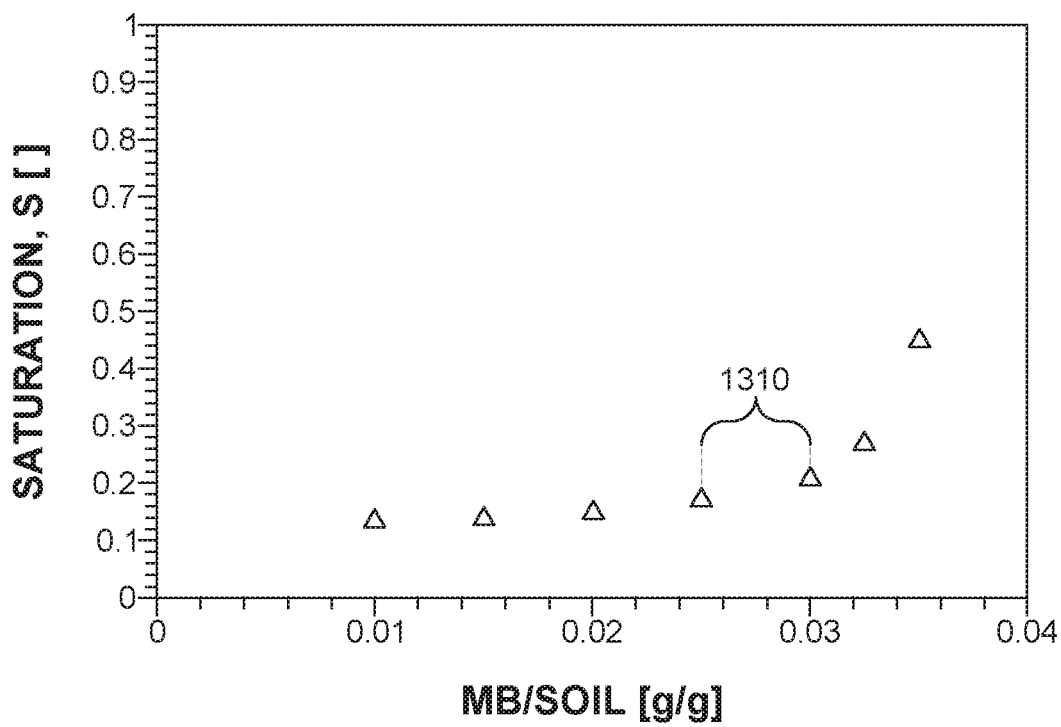

The average RGB intensity values recorded by the smartphone (see FIG. 13A) for each cuvette were converted by the processor of the smartphone, using equations (2) to (7), to the HSV values (see FIG. 13B which shows only the saturation S) for each concentration. There will be excess of dye in the solution after a monolayer of dye is adsorbed around the soil particles and forms the full layer 216. The sudden increase in saturation S corresponds to the transition point between the end of the adsorption of the first full layer (illustrated in FIG. 2B) and the beginning of the excess dye condition (illustrated in FIG. 2C). FIG. 13B shows typical results obtained for kaolinite using Methylene blue and region 1310, at which the saturation S experiences the sudden change, which is assumed to correspond to the point where the full layer 216 of dye has been formed around the soil material, is used to calculated the specific surface area. The region 1310 is referred to herein as the dye excess value because in this region, more dye is attaching to the full layer 216, i.e., the dye becomes excessive. This value is extracted by the processor of the smartphone and used in equation (1) to determine the specific surface area for the tested soil material. More specifically, the processor determines when the sudden change in the saturation S occurs, and for this value, extracts the mass ratio of the dye to sample, which is plotted on the X axis in FIG. 13B. This mass ratio is then used in equation (1) to calculate the specific surface area. In one application, Matlab and ImageJ software were used for all image analysis.

Figure 14:
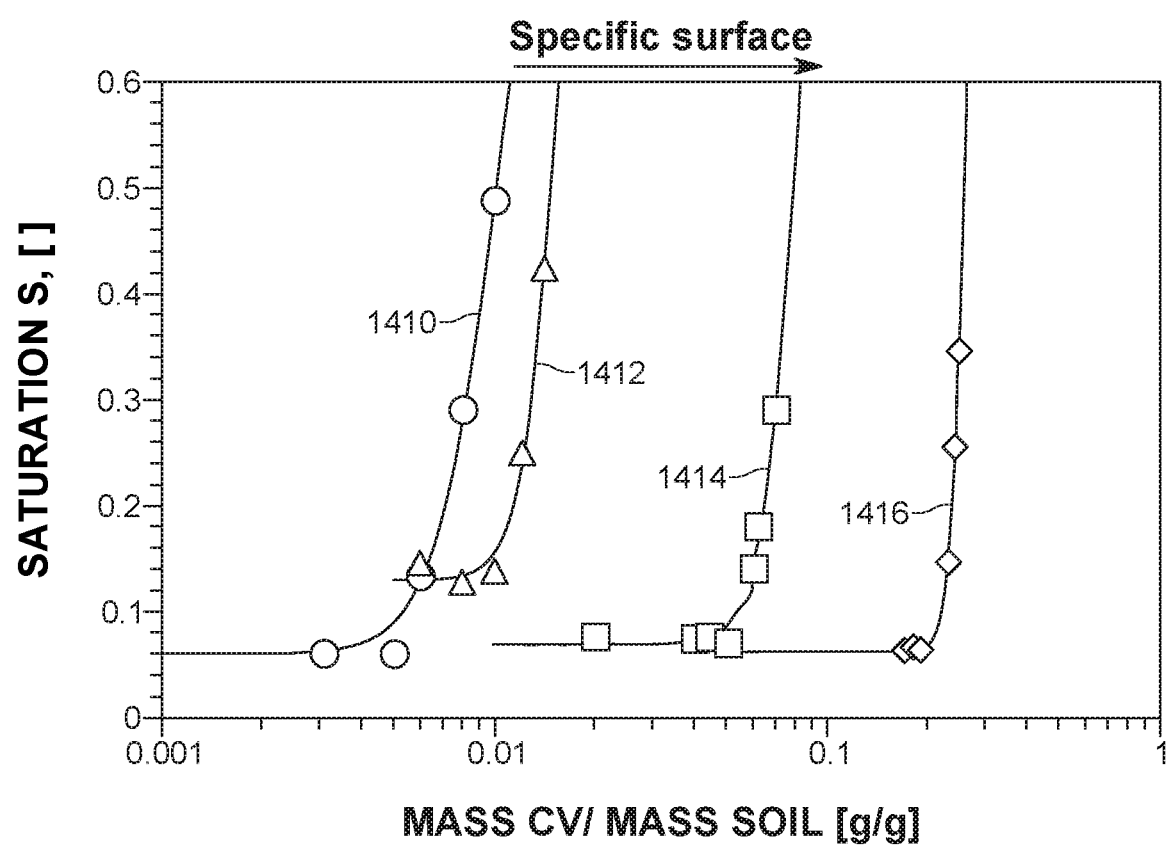
FIG. 14 illustrates the crystal violet adsorption for various materials.

After all the soil samples were tested using the four dyes, the results for the four sediment samples (kaolinite (1) described by curve 1410, kaolinite (2) described by curve 1412, attapulguite described by curve 1414, and bentonite described by curve 1416) with the crystal violet adsorption were plotted in FIG. 14. It is noted in this figure that the saturation S rises with an increase in the amount of dye adsorbed by the soil sample. Each curve shows a clear region where the saturation S suddenly changes.

Figure 15:
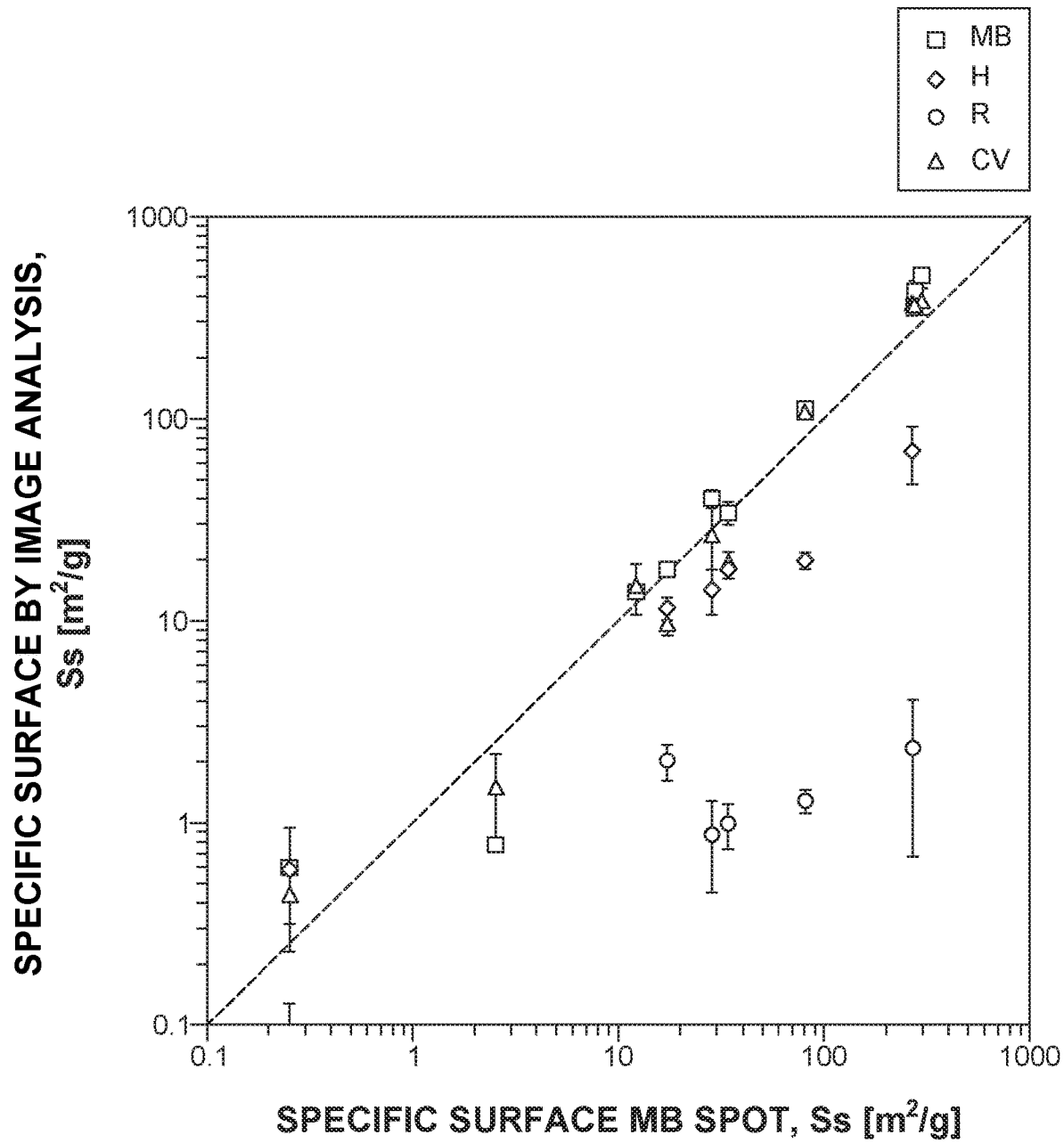
FIG. 15 illustrates specific surface area measurements obtained with the novel image analysis method and the MB spot method.

FIG. 15 compares specific surface area values determined using the novel image analysis for the four dyes, with the values obtained using the standard Methylene blue spot test (naked eye). Results from the latter test showed higher levels of adsorption in comparison to the other dyes. This might result from an overestimation of the contact area due to the tilting of the Methylene blue molecule during adsorption. When the contact area of the Methylene blue was reduced to 66 Å$^2$ per molecule, and the specific surface area was recalculated with this value, the results obtained with the Methylene blue and Crystal Violet agree. The Rhodamine-B and Hemoglobin produced considerably lower results, which may relate to the pH sensitivity. The adsorption of the dye is controlled by the collision frequency and the surface coverage. The collision frequency in liquids is concentration dependent. The higher the concentration, the higher the rate of adsorption.

The above observations are indicative of the influence of the molecular structure and size of dyes on adsorption and its implications for the specific surface area determination. The higher specific surface area values of Methylene blue adsorption result from the shape of the molecule and the tilted adsorption that occurs when the dye concentration is high. In these cases, there is a high cation exchange capacity.

A Methylene blue molecule has dimensions of 17.0×7.6×3.25 Å. It is possible to obtain an optimum adsorption when the particle surfaces are effectively covered by Methylene blue ions lying on the face, 17.0×7.6=130 Å$^2$. An exchange can also occur on the alternate face (17.0×3.25=55 Å$^2$) when the Na+ ions are fully charged. If the longest axis where the smallest face is 24 Å$^2$, and the molecule is tilted at 65-70° with respect to the surface of the particle, the effective area each molecule is 66 Å$^2$, as selected above.

Crystal violet has a more regular shape and results in more accurate contact area calculations. It is also less sensitive to pH changes and it is more suitable to calculate the specific surface area based on the amount of dye adsorption. Rhodamine-B and Hemoglobin adsorption are very sensitive to changes in pH. This might result in poor adsorption and lead to inaccurate specific surface area calculations. These results indicate that the time and pH conditions should be controlled to ensure the reliability and validity of the test.

Water-based testing methods are ideal for swelling clays and fine-grained soils and can measure the internal surface area of phyllosilicates. In dry conditions, the phyllosilicates collapse and the internal surface area cannot be measured. Some soils contain soluble materials that dissolve and color the water (i.e., some marine sediments, residual soils with high Iron Oxide content and organic soils). To apply the proposed methodology to these soils, the background saturation (soil and water without dye) should be also considered.

The inventors have concluded that the specific surface area is a soil index property that controls the behavior related to the surface phenomena. The specific surface area can be measured in fine-grained sediments based on dye monolayer formation, by calculating the amount of dye adsorbed onto the particles. An increase in the saturation S value can identify the transition point between no excess and excessive dye concentrations. The transition can be identified by a colorimeter or spectrometer. The choice of the adsorbate dye has implications for technique optimization, reliability, and validity. Some considerations that need to be taken into account are the shape and size of the dye molecule, the contact area and sensitivity to pH. Water-based methods are ideal for swelling clays and fine-grained soils and can measure the internal surface area of the phyllosilicates.

A novel method to measure the specific surface area in fine-grained soils was proposed herein with a focus on the applicability to engineering. This method combines the physics of dye adsorption with image analysis techniques. The resolution extends from 1 to 700 m$^2$/g. This methodology can be incorporated into routine geotechnical laboratory characterization surveys, for example, as a mobile app.

In one embodiment, the region 1310 (see FIG. 16A) at which the saturation S experiences the sudden change can be determined based on a mathematical function f. In this embodiment, a four parameter logistic function f is discussed. The four parameter logistic function f in this embodiment is selected to be the sigmoidal function, which is defined as:

$$f(x) = a + \frac{d-a}{1 + \left(\frac{x}{c}\right)^{-b}}, \quad (10)$$

where a, b, c, and d are the four parameters.

Figure 16A:
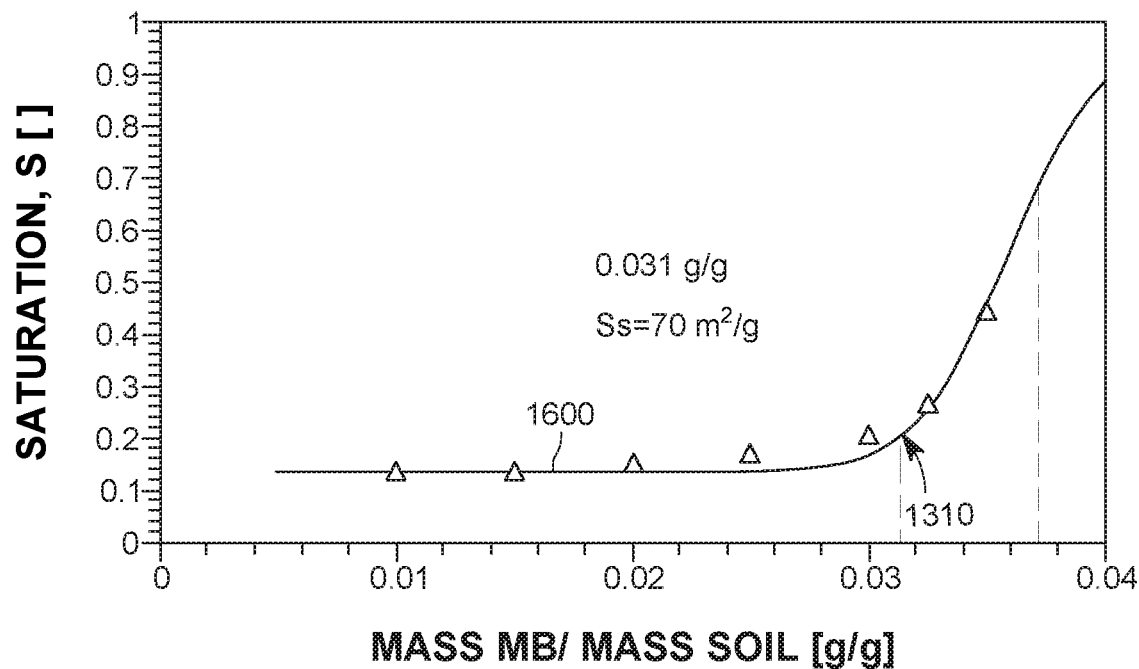
FIG. 16A illustrates a four parameters logistic function that is fitted on the measured saturation S values and FIG. 16B shows a curvature function calculated based on the logistic function for identifying a point of excess dye.
Figure 16B:
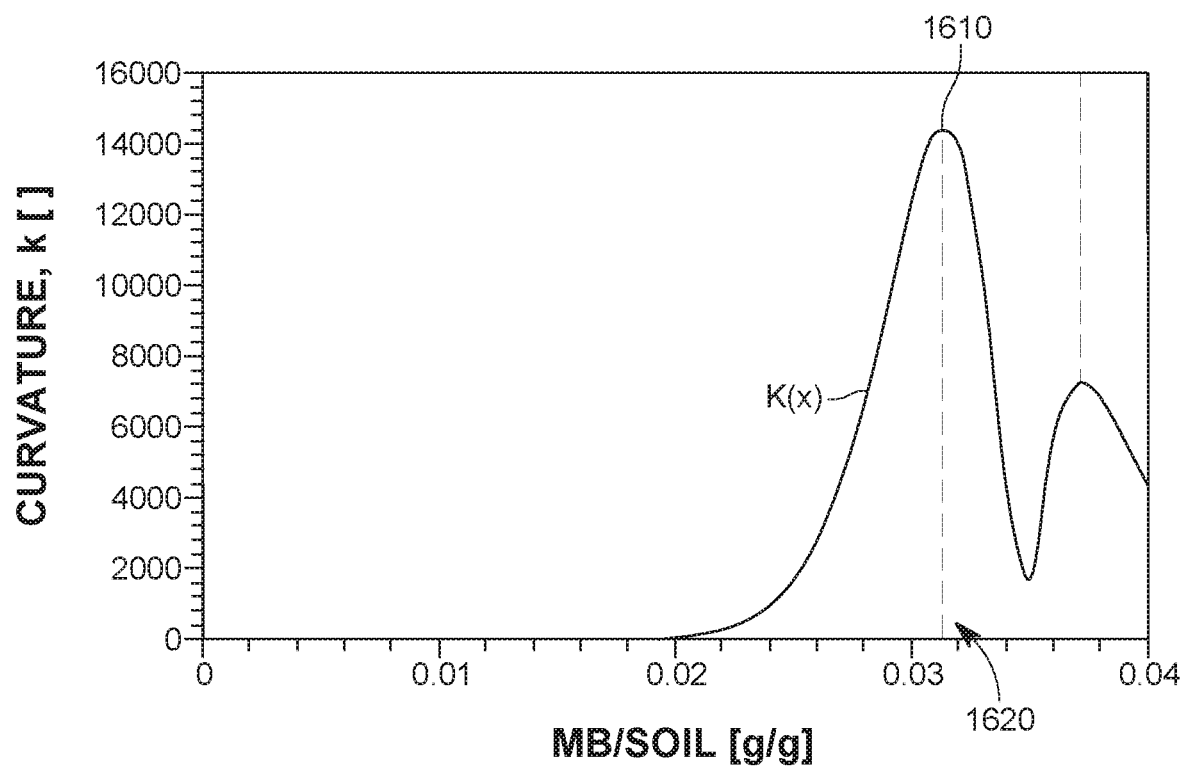

FIG. 16A illustrates the measured saturation S for various mass ratios of a given dye and soil material. A curvature k(x) of the four parameter logistic function f(x) is defined as follows:

$$k(x) = \frac{|f''(x)|}{(1 + f'(x)^2)^{3/2}}. \quad (10)$$

where f' is the first derivative with x, and f'' is the second derivative with x. The maxim curvature is when the derivative of the curvature k'(x)=0. The function f is fitted on the curve 1600 and the parameters a, b, c, and d are calculated. Then, as shown in FIG. 16B, the curvature k(x) is plotted versus the mass ratio of the dye and the soil and based on this curve, the first derivative of the curvature, when made to be zero, as described by point 1610, provides the actual mass ratio 1620 that corresponds to the sudden change in the saturation S. This value is read from the graph shown in FIG. 16B and used in equation (1) to calculate the specific surface area of the soil. While this example has used the sigmoidal function f as an example, other functions may be used as would be appreciated by those skilled in the art.

Figure 17:
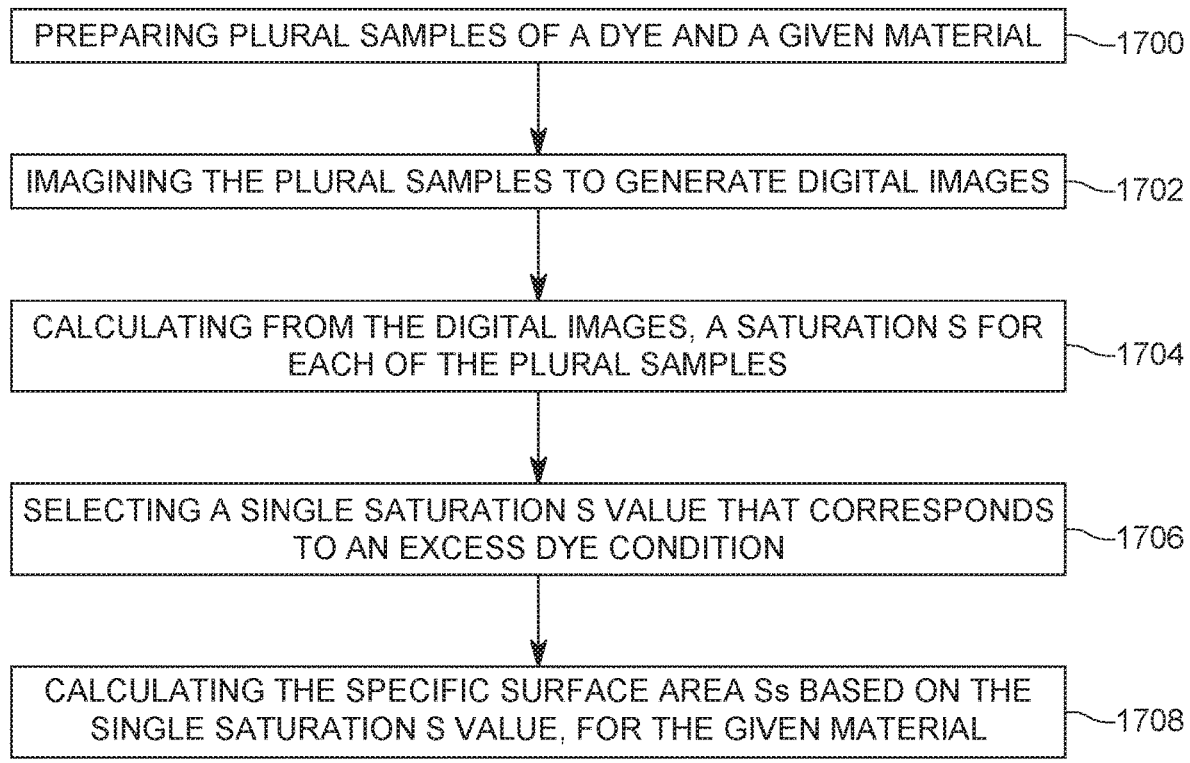
FIG. 17 is a flowchart of a method for measuring the specific surface area of a given material by using a dye and a portable device.
Figure 18:
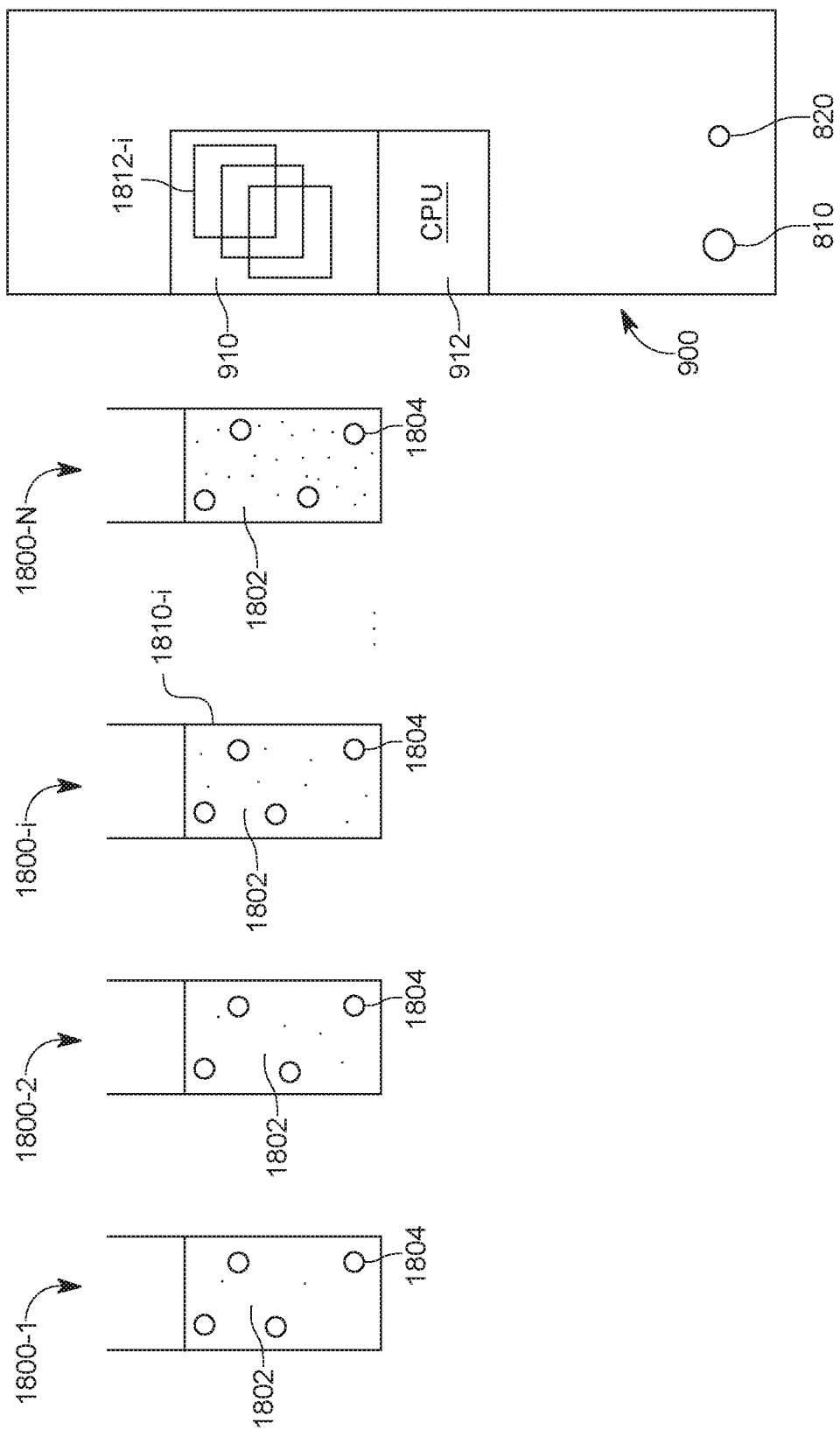
FIG. 18 illustrates a system in which a portable device is used to determine the specific surface area of a given material by taking images of various samples of the given material mixed with a dye in various concentrations.

A method for determining a specific surface area of a given material is now discussed with regard to FIGS. 17 and 18. The method uses the observations and mathematics discussed above. The method includes a step 1700 of preparing N (i.e., plural) samples 1800-*i* (with i being an integer having a value up to N, where N is any integer number larger than 2) of a dye 1802 and a given material 1804. As schematically illustrated in FIG. 18, the dye concentration increases from left to right and each sample 1800-*i* may be stored in a corresponding transparent container 1810-*i*. The method further includes a step 1702 of imaging the plural samples 1800-*i* to generate digital images 1812-*i*. The digital images may be obtained with the digital camera 810, which is part of the smartphone 900. The digital images may be stored in a memory 910, which is also part of the smartphone 900. In one application, the source light 820 of the smartphone 900 is used to illuminate the plural samples 1800-*i* of the dye 1802 and the given material 1804.

The method then calculates in step 1704, from the digital images 1812-*i*, the RGB intensity values and then transforms these values to corresponding HSV values, based on equations (2) to (7). Thus, the processor obtains a saturation S for each of the plural samples 1800-*i*. These calculations may be performed in a processor 912 of the smartphone 900. While this method is discussed herein as being performed by the smartphone 900, one skilled in the art would understand that any computing device may be used to perform this method. In one example, as illustrated in FIGS. 8A and 8B, the method may be performed by a system 800 made of various distinct components that are not integrated into a single device.

The method further includes a step 1706 of selecting a single saturation S value that corresponds to an excess dye condition 1310, as illustrated in FIGS. 16A and 16B. Then, the method calculates in step 1708 the specific surface area $S_s$ based on the single saturation S value, for the given material, as shown in FIG. 16B and based on equation (1).

More specifically, the step of calculating the saturation S includes a step of obtaining from the digital images, intensities associated to green, red and blue colors, and a step of transforming the green, red and blue intensities into saturation S, value V, and hue H values. The method may further include a step of selecting from the saturation S values for the plural samples, the single saturation S value using a parametric function f, a step of fitting the parametric function f onto a graph of the saturation S values, a step of calculating a curvature function k based on the parametric function f, and a step of associating the single saturation S value with a value where a first derivative of the curvature function k is zero. The step of calculating the specific surface area may include a step of mapping the single saturation S value to a ratio of a dye mass to a material mass, and a step of calculating the specific surface area $S_s$ as being proportional to the ratio of the dye mass to the material mass. The step of imagining may include using a digital camera of to obtain the digital images, and storing the digital images on a memory.

The method may further include using a processor programmed according to an app to perform the step of calculating the saturation S, the step of selecting the single saturation S value, and the step of calculating the specific surface area $S_s$, where the processor, the digital camera, and the memory are part of the smartphone 900. The step of preparing may include a step of mixing the dye with the given material to obtain various ratios of the dye mass to the material mass.

The steps discussed above may be performed in any order and they may be combined in any configuration, i.e., in one device only part of the steps are implemented while in another device, more or less of the steps are implemented.

The disclosed embodiments provide a method and device for calculating a specific surface area of a material based on a calculated saturation from imagining processing. It should be understood that this description is not intended to limit the invention. On the contrary, the embodiments are intended to cover alternatives, modifications and equivalents, which are included in the spirit and scope of the invention as defined by the appended claims. Further, in the detailed description of the embodiments, numerous specific details are set forth in order to provide a comprehensive understanding of the claimed invention. However, one skilled in the art would understand that various embodiments may be practiced without such specific details.

Although the features and elements of the present embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A method for determining a specific surface area of a given material, the method comprising:
   preparing plural samples of a dye and the given material;
   imagining the plural samples to generate digital images;
   calculating from the digital images, a saturation S for each of the plural samples;
   selecting a single saturation S value that corresponds to an excess dye condition; and
   calculating the specific surface area $S_s$ based on the single saturation S value, for the given material.

2. The method of claim 1, wherein the step of calculating the saturation S comprises:
   obtaining from the digital images, intensities associated to green, red and blue colors; and
   transforming the green, red and blue intensities into saturation S, value V, and hue H values.

3. The method of claim 2, further comprising:
   selecting from the saturation S values for the plural samples, the single saturation S value using a parametric function f.

4. The method of claim 3, further comprising:
   fitting the parametric function f onto a graph of the saturation S values;
   calculating a curvature function k based on the parametric function f; and
   associating the single saturation S value with a value where a first derivative of the curvature function k is zero.

5. The method of claim 1, wherein the step of calculating the specific surface area $S_s$ comprises:
   mapping the single saturation S value to a ratio of a dye mass to a material mass; and
   calculating the specific surface area $S_s$ as being proportional to the ratio of the dye mass to the material mass.

6. The method of claim 1, wherein the step of imagining comprises:
   using a digital camera to obtain the digital images; and
   storing the digital images on a memory.

7. The method of claim 6, further comprising:
   using a processor programmed according to an app to perform the step of calculating the saturation S, the step of selecting the single saturation S value, and the step of calculating the specific surface area $S_s$,
   wherein the processor, the digital camera, and the memory are part of a smartphone.

8. The method of claim 1, wherein the step of preparing comprises:
   mixing the dye with the given material to obtain various ratios of the dye mass to the material mass.

9. A portable device for determining a specific surface area of a given material, the portable device comprising:
   a source light configured to illuminate plural samples of a dye and the given material;
   a digital camera configured to imagine the plural samples to generate digital images; and
   a processor that is connected to the digital camera, the processor being configured to,
   calculate from the digital images, a saturation S for each of the plural samples,
   select a single saturation S value that corresponds to an excess dye condition, and
   calculate the specific surface area $S_s$ based on the single saturation S value, for the given material.

10. The portable device of claim 9, wherein the processor is further configured to:
   obtain from the digital images, intensities associated to green, red and blue colors, and
   transform the green, red and blue intensities into saturation S, value V, and hue H values.

11. The portable device of claim 10, wherein the processor is further configured to:
   select from the saturation S values for the plural samples, the single saturation S value using a parametric function f.

12. The portable device of claim 11, wherein the processor is further configured to:
   fit the parametric function f onto a graph of the saturation S values;
   calculate a curvature function k based on the parametric function f; and
   associate the single saturation S value with a value where a first derivative of the curvature function k is zero.

13. The portable device of claim 9, wherein the processor is further configured to:
   map the single saturation S value to a ratio of a dye mass to a material mass; and
   calculate the specific surface area $S_s$ as being proportional to the ratio of the dye mass to the material mass.

14. The portable device of claim 9, wherein the processor is further configured to:
   use the digital camera to obtain the digital images; and
   store the digital images on a memory.

15. The portable device of claim 14, wherein the processor is further configured to:
   use an app to perform the step of calculating the saturation S, the step of selecting the single saturation S value, and the step of calculating the specific surface area $S_s$.

16. The portable device of claim 9, wherein the plural samples are obtained by mixing the dye with the given material to obtain various ratios of the dye mass to the material mass.

17. The portable device of claim 16, wherein the various ratios of the dye mass to the material mass are input to the processor.

18. A method for determining a specific surface area of a material, the method comprising:
   imagining plural samples of a dye mixed with the material to generate digital images;
   calculating from the digital images, saturation S values for the plural samples;
   calculating a single saturation S value that corresponds to an excess dye condition; and
   calculating the specific surface area $S_s$ based on the single saturation S value, for the given material.

19. The method of claim 18, further comprising:
   fitting a parametric function f onto a graph of the saturation S values;
   calculating a curvature function k based on the parametric function f; and
   associating the single saturation S value with a value where a first derivative of the curvature function k is zero.

20. The method of claim 19, further comprising:
   mapping the single saturation S value to a ratio of a dye mass to a material mass; and
   calculating the specific surface area $S_s$ as being proportional to the ratio of the dye mass to the material mass.

* * * * *